US000001282H

United States Statutory Invention Registration [19]

[11] Reg. Number: H1282

Joyce et al.

[43] Published: Feb. 1, 1994

[54] FLUIDIC VOLUME-CYCLED RESPIRATOR

[75] Inventors: James W. Joyce, Rockville; George Mon, Potomac, both of Md.

[73] Assignee: The United States of America as represented by the Secretary of the Army, Washington, D.C.

[21] Appl. No.: 474,603

[22] Filed: Feb. 5, 1990

[51] Int. Cl.[5] ..... A61M 16/00

[52] U.S. Cl. ..... 128/204.23; 128/204.24

[58] Field of Search ..... 128/204.18, 204.23, 128/204.26, 204.21; 137/821, 820; 73/861.19

[56] References Cited

U.S. PATENT DOCUMENTS

| | | | |
|---|---|---|---|
| 3,379,194 | 4/1968 | Ziermann | 128/204.24 |
| 3,682,189 | 8/1972 | Lapinas et al. | 137/821 |
| 3,684,166 | 8/1972 | Kruger | 137/821 |
| 3,714,828 | 2/1973 | Durkan | 137/821 |
| 3,896,800 | 7/1975 | Cibulka | 128/145.8 |
| 3,976,065 | 8/1976 | Durkan | 128/204.24 |
| 3,981,301 | 9/1976 | Warnow et al. | 128/204.24 |
| 4,019,382 | 4/1977 | El-Gammal | 128/2.08 |
| 4,054,133 | 10/1977 | Myers | 128/142.2 |
| 4,057,059 | 11/1977 | Reid, Jr. et al. | 128/204.24 |
| 4,120,300 | 10/1978 | Tiep | 128/204.24 |
| 4,232,668 | 11/1980 | Strupat | 128/204.24 |
| 4,241,732 | 12/1980 | Berndtsson | 128/204.24 |
| 4,278,110 | 7/1981 | Price et al. | 128/204.21 |
| 4,289,126 | 9/1981 | Seireg et al. | 128/204.24 |
| 4,381,002 | 4/1983 | Mon | 128/204.24 |
| 4,414,982 | 11/1983 | Durkan | 128/716 |
| 4,448,192 | 5/1984 | Stawitcke et al. | 128/204.21 |
| 4,461,293 | 7/1984 | Chen | 128/204.23 |
| 4,462,398 | 7/1984 | Durkan et al. | 128/200.14 |
| 4,471,773 | 9/1984 | Bunnell et al. | 128/204.21 |
| 4,506,666 | 3/1985 | Durkan | 128/204.23 |
| 4,519,387 | 5/1985 | Durkan et al. | 128/204.23 |
| 4,533,346 | 8/1985 | Cosgrove, Jr. et al. | 128/204.21 |
| 4,570,631 | 2/1986 | Durkan | 128/204.23 |
| 4,584,996 | 4/1986 | Blum | 128/204.21 |
| 4,587,967 | 5/1986 | Chu et al. | 128/204.21 |
| 4,611,590 | 9/1986 | Ryschka et al. | 128/204.21 |
| 4,617,637 | 10/1986 | Chu et al. | 128/204.21 |
| 4,644,781 | 2/1987 | Mon | 137/820 |
| 4,705,034 | 11/1987 | Perkins | 128/204.21 |
| 4,747,403 | 5/1988 | Gluck et al. | 128/204.21 |
| 4,766,894 | 8/1988 | Legrand et al. | 128/204.21 |
| 4,823,788 | 4/1989 | Smith et al. | 128/204.21 |
| 4,838,259 | 6/1989 | Gluck et al. | 128/204.21 |
| 4,877,023 | 10/1989 | Zalkin | 128/204.21 |
| 4,971,049 | 11/1990 | Rotariu et al. | 128/204.21 |

OTHER PUBLICATIONS

Davison, E. L., "Application of Fluidics in Medical Breathing Apparatus", *Fluidics Quarterly*, pp. 11–26.

*Primary Examiner*—David H. Brown

*Attorney, Agent, or Firm*—Saul Elbaum; Freda L. Krosnick

[57] ABSTRACT

A fluidic, volume-cycled respirator circuit comprising a fluidic flowmeter, a tidal volume selection controller and an inlet valve. The flowmeter is connected to the controller through a transmitting means which transmits gas flow frequency signals. Said controller is then connected to the inlet valve, which is connected back to the flowmeter; hence, the respirator circuit is complete. The tidal volume selection controller may operate by either fluidics, electronics, or the combination of the two. The flowmeter facilitates supply of air to the patient. The amount of air supplied is controlled by the tidal volume selection controller which senses inspiration and gas flow frequency. The controller is equipped with a timer back-up system in the event that either the system or the patient fail to respond. The valve is operated at the direction of the tidal volume selection controller. The valve is open during the inspiratory phase and closed during the exhalation phase. The respirator herein overcomes the use of burdensome piston-bellows assemblies, has few moving parts and is relatively small in size. The use of piston-bellows assemblies is avoided by the use of a fluidic oscillator flowmeter.

6 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FLUIDIC VOLUME-CYCLED RESPIRATOR

RIGHTS OF THE GOVERNMENT

The invention described herein may be manufactured, used and licensed by or for the U.S. Government without payment to us of any royalty thereon.

BACKGROUND OF THE INVENTION

Volume-cycled respirators which have been used in the past and those which are presently in use are cumbersome in nature. Most of them make use of piston-bellows assemblies to deliver the tidal volumes of breathing gas to the patient. Conventional respirators are fairly complex and further employ a variety of elements including snap valves, springs, solenoid valves, magnets, gear boxes, ratchets, mechanical linkages, pulleys, photocells, electronic circuitry, and other components to provide a number of functions. The complexity and hybrid nature of these systems results in large, massive and expensive respirator units which are somewhat fragile and susceptible to mechanical failure. Basically, most of them have numerous moving parts which makes the apparatus more complex to operate and maintain.

The present invention relates to a fluidic volume-cycled respirator circuit which is relatively simple in its construction; contains few, if any, moving parts; is highly efficient; and is convenient to use and transport. The respirator herein basically comprises an input valve, a flowmeter and a controller.

In order to better understand the present invention, one should understand the prior art teachings in the field of respirators.

Respirators comprising (1) a control circuit which is responsive to a (2) sensor are taught by Durkan and Durkan et al. in U.S. Pat. Nos. 4,462,398; 4,506,666; 4,519,387 and 4,570,631. The control circuits described therein operate an input valve. The sensor picks up the negative pressure sensed from the patient using the respirator. The sensor then, in accordance with its sensing of the negative pressure, instructs the control circuit to operate the input valve in response to the patients' needs. The control circuit may also operate the valve if no negative pressure is sensed within a predetermined time period. Hence, the respirator disclosed operates based on the change in pressure from the patient and based on a predetermined time set to control the supply valve. Note that the patents may additionally make use of a conventional flowmeter. The sensor taught may be fluidic; and the valve is electrically controlled by the control circuit. The patents further teach generally that other fluidic elements can be used in their respirator circuit.

The Durkan and Durkan et al. references discussed above are very elaborate breathing devices. They make use of both fluidics and electronics in their sensor means and control circuits. The fluidic devices are fluidic amplifiers. Based on the description of the Durkan patients above it may appear that these references teach our invention. This is not so because our invention is able to provide the same service as Durkan but using a more reliable and compact system. The respirator herein is not as complex as those taught by these patent references. Moreover, our invention makes use of fluidic oscillators, as opposed to fluidic amplifiers. The use of one is not an obvious sustitution or modification for the use of the other.

U.S. Pat. No. 4,461,293, issued to Chen, teaches a breathing apparatus similar to that taught by Durkan. In this teaching, a control circuit is responsive to a sensor which operates a valve to supply breathing gas to a patient. This system, however, is a more complex system than that of the present invention. Moreover, unlike the teaching in Chen, the present invention makes use of a fluidic oscillator as the flowmeter as opposed to a fluidic amplifier.

Perkins, U.S. Pat. No. 4,705,034, teaches a respiratory apparatus which may use fluidic sensors—note, column 4, lines 49–65. Sensors of this type are able to detect the onset of inhalation and the volume metering of the breathing gas. The respirator taught by Perkins is a demand system which requires the use of an electrical solenoid to activate the input valve. In addition, the metering system therein has many moving parts. This system makes use of a piston which our invention avoids. Perkins teaches a much more elaborate system than that of the present invention.

U.S. Pat. No. 4,054,133, issued to Myers, teaches a respirator apparatus that comprises a control means which is responsive to inhalation, pause and exhalation of a patient. Its response regulates the flow of oxygen from a supply chamber to said patient. Reduced pressure activates an input valve to only allow oxygen flow during inhalation. This breathing apparatus makes use of a diaphragm to sense the pressure differential due to the patient's breathing. In addition, nowhere does Myers indicate any use of fluidics in his breathing device.

U.S. Pat. No. 4,381,002, issued to Mon, one of the inventors herein, teaches a respirator which comprises a valve, a fluidic control system which senses inspiration and exhalation, and an oxygen source. This patent, however, does not mention the use of a fluidic flowmeter. Moreover, the Mon respirator makes use of a diaphragm and a fluidic amplifier controller, neither of which is within the scope of the present invention.

U.S. Pat. No. 4,278,110, issued to Price et al., claims a respirator which utilizes a fluidic valve, a flowmeter, a flow controller which senses expiration and inspiration, and an oxygen source. The oxygen is supplied on a demand basis only. A fluidic oscillator is not use in Price et al. Moreover, our invention does not require the use of a fluidic valve.

U.S. Pat. No. 3,896,800 teaches that the use of fluidic and electronic respirator control devices is well known. The apparatus taught, however, requires the use of a diaphragm.

U.S. Pat. No. 4,019,382, issued to El-Gammal, sets forth the general teaching of the well-known use of a fluidic flowmeter which measures respiratory functions. Note that the flowmeter is for use with cumbersome breathing apparatus. The breathing apparatus does not teach the respirator circuit claimed herein.

U.S. Pat. Nos. 4,120,300; 4,289,126 and 4,414,982 are recited to give the reader more background on the general teachings of the use of fluidics in the respirator art areas.

The use of fluidics in respirators is not a novel one. Note, "Respiratory Care Applications for Fluidics," *Respiratory Therapy*, pp. 29–32 (1973).

As one may note from the teachings in the prior art with regard to respirators, the individual concepts of using fluidics, control devices, sensors, etc. are not novel. More particularly, the use of fluidic control systems and fluidic sensors are further well known. However, the combination of these concepts are neither taught nor suggested in the prior respirator art.

It is the combination of these general components which result in the hand-held respirator of the present invention.

BRIEF SUMMARY OF THE INVENTION

This invention deals with a fluidic, volume-cycled respirator circuit comprising a fluidic oscillator flowmeter, a pressure transducer, a tidal volume selection controller and an inlet valve. The flowmeter is connected through a pressure transducer or microphone to the controller, which is in turn connected to the inlet valve, which is further connected back to the flowmeter. Hence, the respirator circuit is complete. The tidal volume selection controller may operate by either fluidics, electronics, or a combination of the two. Electronic tidal volume selection controllers are preferred. The flowmeter facilitates the supply of air to the patient. The amount of air supplied is controlled by the tidal volume selection controller which senses the inspiration phase, exhalation phase of the patient's breathing, and gas flow frequency passing through the flowmeter. Upon inspiration or exhalation, the valve is operated at the direction of the tidal volume selection controller to accommodate the needs of the patient. The valve is instructed to open during the inspiratory phase and instructed to close during the exhalation phase. The valve is additionally closed once a specific, programmed breathing gas glow frequency has been met. This will be further discussed below.

When the respirator circuit of the present invention is in use, a pressurized breathing gas is forced through the inlet valve which is open during the inspiratory phase of the patient's breathing and is closed during his exhalation phase. The breathing gas then continues through the inlet valve to a fluidic flowmeter and to the patient in need. The flowrate of the gas is converted to a frequency signal by the flowmeter. The frequency signal is monitored by a pressure transducer or a microphone which is connected to a controller. Once the controller translates the incoming signals to accommodate the needs of the patient, it directs the input valve to either open or close, thus regulating the amount of breathing gas entering the system. The controller is further able to detect inspiration of the patient. Inspiration is detected by the device sensing a change in pressure of the air passing therethrough due to the patient'S spontaneous breathing. When inspiration of the patient is detected, the controller instructs the opening of the input valve.

The controlling device may, optionally, contain a conventional electronic timing circuit which would enable the controller to dictate the exhalation phase of the breathing cycle to be within preselected time limitations. This timing circuit may override the spontaneous response or lack of response of the patient.

The fluidic volume-cycled respirator circuit system of the present invention requires that the flowmeter therein be fluidic in nature. This is critical to the invention. The controlling means, on the other hand, may operate either by fluidics, electronics or a combination of the two. Use of an electronic controlling means is preferred.

Unlike the majority of volume-cycled respiratory devices already on the market, the volume-cycled respirator of the present invention eliminates the use of pistons, bellows and other cumbersome component parts. The respirator herein is basic in nature and operates efficiently using and containing only essential components.

The volume-cycled respirator herein is both reliable and efficient in its operation. It contains few moving parts, if any; and it is essentially maintenance free. Moreover, it is a convenient device to use and carry. Note, that the respirator is relatively small in size—about pocket-size.

It is an object of the present invention to provide an efficient and reliable respirator.

It is a further object of the present invention to provide a respirator which is light weight.

It is a further object of the present invention to provide a respirator which is convenient to operate and carry.

It is a further object of the invention to provide a respirator containing few moving parts.

Still a further object of the present invention is to provide a relatively maintenance free respirator.

Other objectives and features of the present invention will be apparent from the following detailed description of the invention, drawings and the claims.

DETAILED DESCRIPTION OF THE INVENTION

The foregoing objectives are achieved by the respirator of the present invention. The present invention deals with a respirator made up primarily of an input valve, a flowmeter and a controller which operates the input valve. This respirator is in a circuit configuration.

Any conventional fluidic, oscillator flowmeter may be used in the invention. The fluidic oscillator creates a closed system in order to accurately measure the flow of breathing gas passed therethrough. Fluidic flowmeters are true volume flowmeters and contain no moving parts. They assist in controlling the inspiratory phase of the breathing cycle. The flowmeter herein replaces the piston/bellows of the prior art respirators. This represents the novelty of our invention.

In addition, any conventional tidal volume selection controller to operate the input valve may be used as the controller. The only critical requirements for said controller is that (1) it be able to detect oscillator frequency signals sent by the flowmeter through a microphone; (2) it be able to detect negative pressure signals sent from the patient and through a pressure sensor tube or device; and (3) it be equipped with a time-cycle time. Based on these requirements, the controller is able to control the input valve according to the method in which it has been programmed by a medical operator. The controller may operate the inlet valve based on a set frequency integration (counter), a set time period or by the spontaneous inspiration of the patient. The controller is equipped with a totalizer/counter which is set to sense a predetermined number of frequency counts. Conventional totalizer/counters such as those manufactured by Redington® Counters, Inc. may be used herein. The counter is one of the programmable features of the present invention. The timer may be set to customize the requirements of the individual patient. The controller is programmed to accommodate the needs of the patient.

More specifically, the fluidic oscillator flowmeter is constructed from a fluidic laminar proportional amplifier having negative feedback. The flowmeter puts out an output pressure signal which has a frequency that is a linear function of the volumetric flow rate of breathing gas sent through the oscillator flowmeter. This relationship of output pressure and frequency is independent of the type of gas flowing therethrough. The relationship is constant regardless of the gas properties—i.e. density and viscosity. Hence, for the type of fluidic oscillator flowmeter, the volumetric flow may be represented as $$Q=Kf; \quad (1)$$

where

Q=volumetric flow f=oscillator frequency; and

K=geometric constant

In order to determine the tidal volume (volume of breathing gas delivered to the patient) of the flowmeter, the flowmeter's volumetric flow output must be integrated over the total time of the inspiratory phase of the breathing cycle; therefore, $$V=\int_O^T Q\,dt; \quad (2)$$

where

V=tidal volume; and

T=total time of inspiratory phase

The equation (2) may be simplified and rewritten as $$V=K\int_O^T f\,dt; \quad (3)$$

by substituting the "Q" with the equivalent "Kf."

The quantity under the integral sign in equation (3) above represents the oscillator frequency counts over the time period T. Therefore, a certain amount of tidal volume corresponds to a specific oscillator frequency count.

The tidal volume selection controller may be either fluidic, electronic or a combination of the two. As discussed above, it senses the oscillator frequency counts and controls the input valve accordingly. For example, if an electronic controller is used, a conventional microphone may be used in the flowmeter to allow the pressure oscillations to be converted into a corresponding electrical signal. The resulting electrical signal can be processed to accurately perform a counting function. Once a certain count quantity is reached, as programmed by an operator, the controller can then send a signal to operate the input valve that controls the supply of breathing gases.

The controller also contains an electronic timing device which controls the breathing cycle in the event that the patient is unable to inhale and cause a negative pressure to signal the valve to open. This electronic timing circuit maintains the phases within the breathing cycle to stay within a preselected time limit by signaling the input valve to either open or close. The preselected time limit is programmed in by the medical operator.

Now that the basic invention has been described, its operation may be understood by the following description. When the breathing gas inlet valve is open, gas is forced through a fluidic oscillator flowmeter which converts the flow rate to a frequency signal. The frequency is proportional to the volume flow rate. The output flow of gas from the flowmeter is delivered to the patient. The frequency signal is then monitored and converted into frequency counts by the use of a transmitting means, such as a microphone. The frequency counts are transmitted to the tidal volume controller which is equipped with a conventional, electronic frequency counter/totalizer which may be programmed. Once the specific oscillator frequency count is reached, the controller signals the input valve to close. This ends the inspiratory phase of the patient's breathing cycle and starts the exhalation phase. The exhalation phase is terminated by an inspiratory effort from the patient. The inspiratory effort is sensed as a negative pressure by a conventional pressure sensor. This negative pressure is communicated to the controller in the form of a slight negative pressure signal, one below ambient pressure—approximately −0.5 to −4.0 cm of water. The tidal volume selection controller then instructs the input valve to open. Hence, a new inspiratory phase is initiated. In the event that the patient is unable to spontaneously inspire, a timer would kick in in order to open the input valve. The timer may be programmed to accommodate the patient. Moreover, the timer may override the other controller functions. For instance, if the patient were to resume his spontaneous inspiration after the timer had kicked in, the timer is constructed in such a manner which would allow the patient's effort to inhale to override the timer device.

In normal operation, each new respiratory cycle will be initiated either when the patient attempts to breath (assist mode), or when the preset timer value is reached (control mode), whichever occurs first. This opens the input valve. The exhalation portion of the respiratory cycle, which occurs during the period in which the input valve is closed, is initiated when a preset frequency count is reached (corresponding to a specific volume of breathing gas), or if the frequency counter malfunctions, when a preset timer value is reached. This closes the input valve.

Other features of the present invention will be apparent from the following drawings and their description.

DETAILED DESCRIPTION OF THE DRAWINGS AND THE INVENTION

Figure 1:
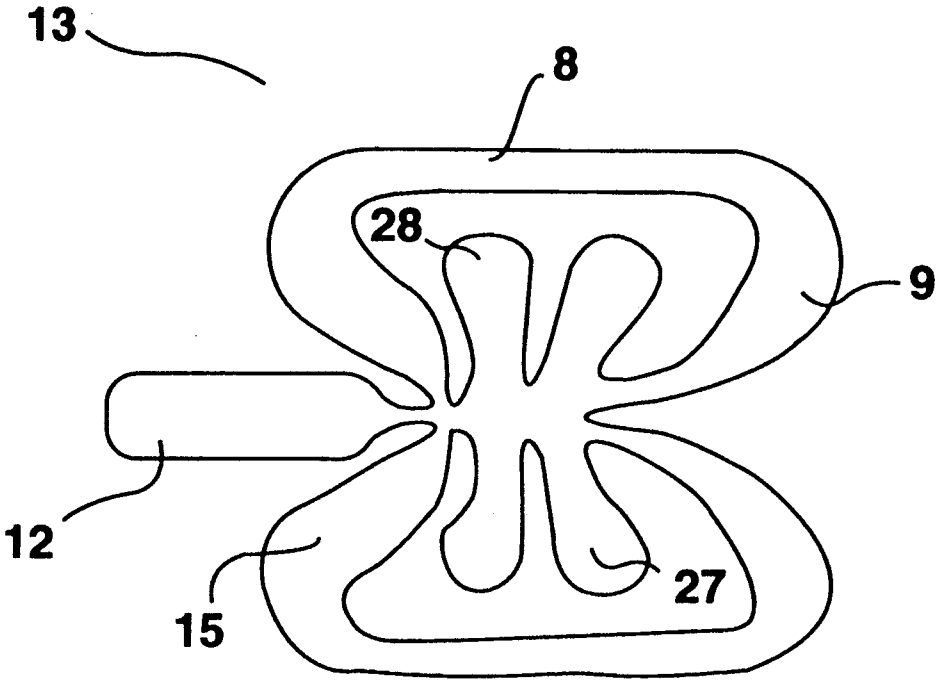
FIG. 1 is a schematic drawing of a fluidic oscillator of the type which may be used in the flowmeter set forth in the volume-cycled respirator of the present invention.

FIG. 1 teaches a schematic representation of a conventional fluidic oscillator 13. Said fluidic oscillator 13 is the type which may be used in the volume-cycled respirator circuit of the present invention. The oscillator 13 comprises supply port 12, vent ports 27 and 28, output ports 9, feedback lines 8, and input ports 15. Input ports 15 recirculate the fluidic flow resulting from the feedback lines 8. This fluidic oscillator 13 measures volume flow rate and is constructed from a fluidic laminar proportional amplifier having negative feedback lines 8.

Figure 2:
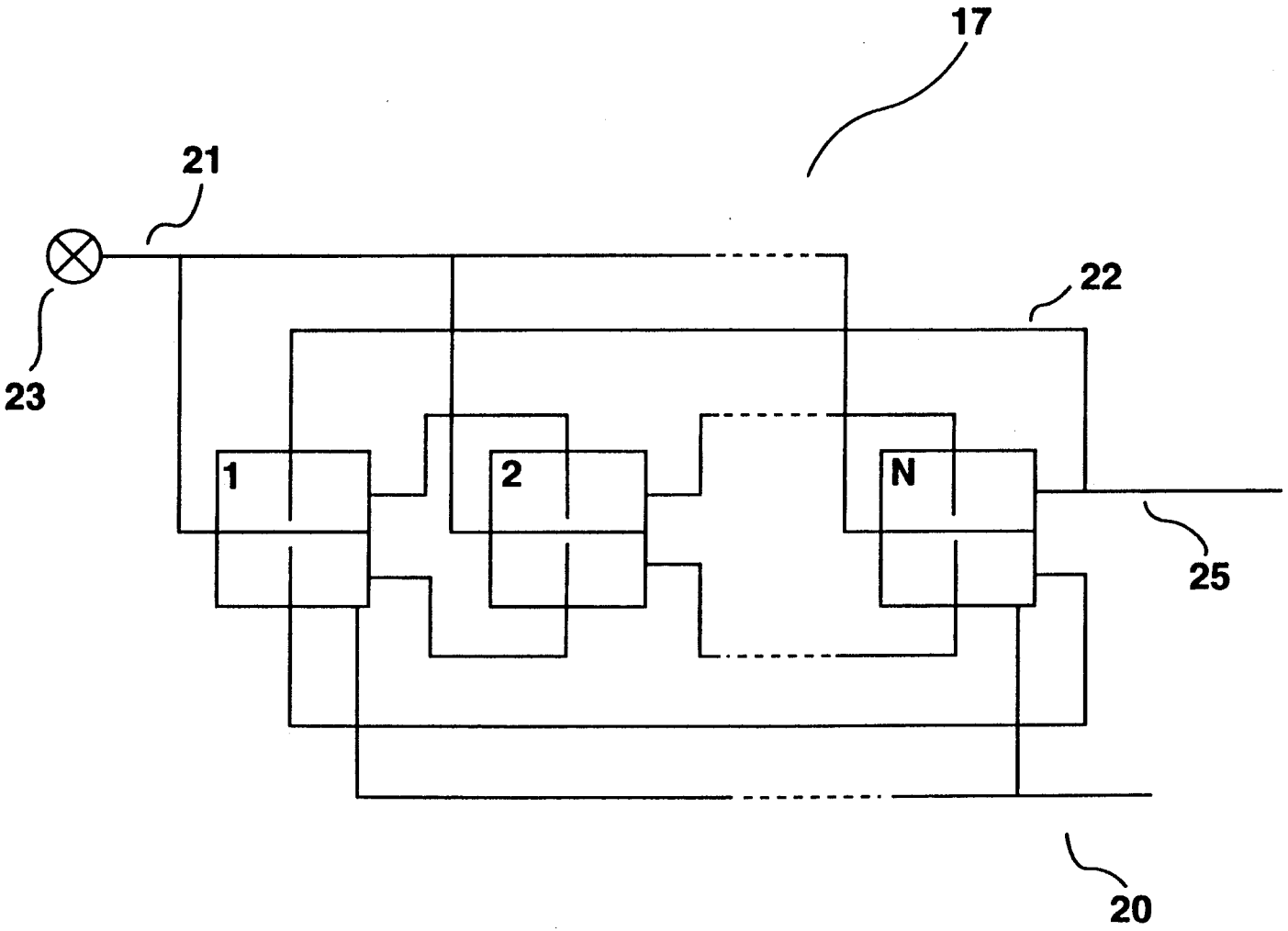
FIG. 2 is a typical oscillator flowmeter circuit comprising a plurality of the fluidic oscillators of FIG. 1. This oscillator flowmeter circuit may be used for the flowmeter in our invention.

FIG. 2 is a schematic representation of a typical flowmeter circuit 17. In said flowmeter circuit 17, from one to N stages of fluidic laminar proportional amplifiers (LPA) having feedback lines may be used to obtain the required flow rates. Note that the LPAs in FIG. 2 are represented as 1, 2 through N. The flowmeter circuit 17 comprises supply port 23 for the breathing gas, input line 21, feedback line 22, frequency output 25, and exit port 20. Said flowmeter circuit 17, and flowmeter circuits of a similar type, may be used in the volume-cycled respirator circuit of the present invention.

Figure 3:
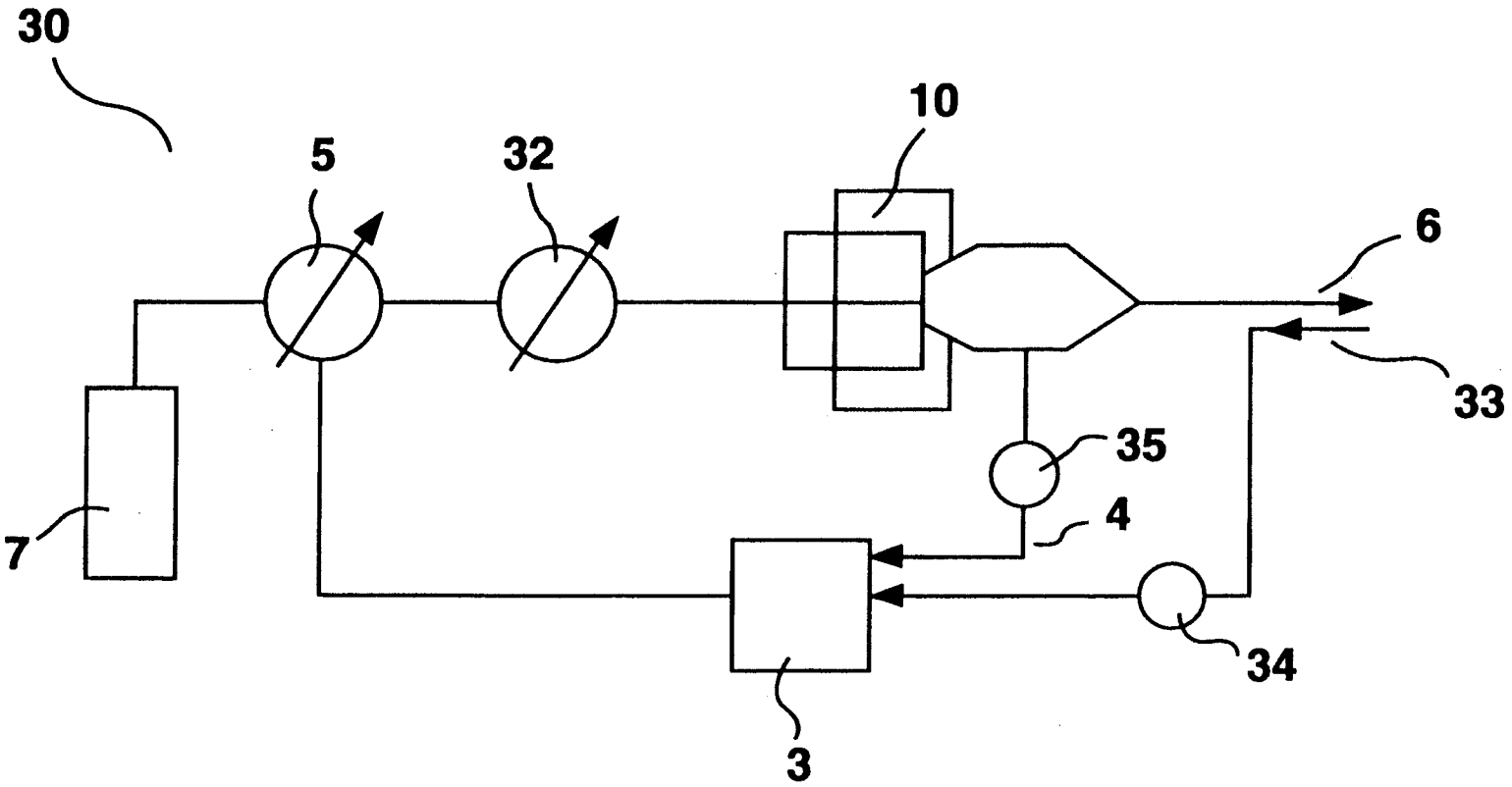
FIG. 3 is a simplified schematic drawing of the volume-cycled respirator circuit of the present invention.

FIG. 3 represents a simplified schematic figure of the volume-cycled respirator of the present invention. The volume-cycled respirator circuit, generally set forth as 30, comprises breathing gas supply 7 which introduces a pressurized breathing gas to the respirator system, control valve 5, conventional pressure regulator 32 fluidic oscillator flowmeter 10, exit line 6 to patient, transmitting line 4 running from the flowmeter 10 through either a pressure transducer or microphone 35 to the tidal volume controller 3. Said controller 3 is connected to control valve 5 to complete the volume-cycled respirator circuit 30. A transmitting line (or tube) 33 running from the patient is connected to pressure sensor 34. This allows the pressure sensor 34 to detect the patient's inspiration effort. Pressure sensor 34 is capable of detecting negative pressure as low as −0.5 to −4.0 cm of water.

The volume-cycled respirator circuit 30 supplies breathing gas to the respirator system at control valve 5. The breathing gas passes through input valve 5 and into fluidic flowmeter 10. The flowmeter 10 facilitates the supply of breathing gas to the patient through output line 6. The patient's breathing response can be transmitted via transmitting line 33 and registered by pressure sensor 34. Pressure sensor 34 is used to detect even extremely minor changes in pressure created by a patient's inspiratory efforts. Once the pressure sensor detects a negative pressure, it communicates said change in pressure to the tidal volume selection controller 3 which in turn sends an output signal which operates input valve 5 to open. The tidal volume selection controller 3 controls the volume of air that enters the volume-cycled respirator 30 by operating the input valve 5.

The tidal volume controller 3 additionally operates the input valve 5 when a set volume of breathing gas has been administered to the patient. The tidal volume controller 3 is equipped with an electronic counter/totalizer which counts the frequency output of the pressure transducer or microphone 35. The tidal volume controller 3 may be programmed by a medical operator to accommodate the personal needs of the patient.

Another avenue in which the tidal volume controller 3 may operate the input valve 5 is by the use of a timing device incorporated into said controller 3. Said timing device may be programmed in order to regulate the exhalation phase of the breathing cycle to be within certain time limits. For example, if for some reason the pressure transducer or microphone 35 is malfunctioning (therefore no frequency output is received by the controller 3) and the patient has no spontaneous breathing (therefore no negative pressure signal is sensed by the controller 3), the timing device within said controller 3 would take over and cause the controller 3 to open and close the input valve 5 during the set timed intervals.

Figure 4:
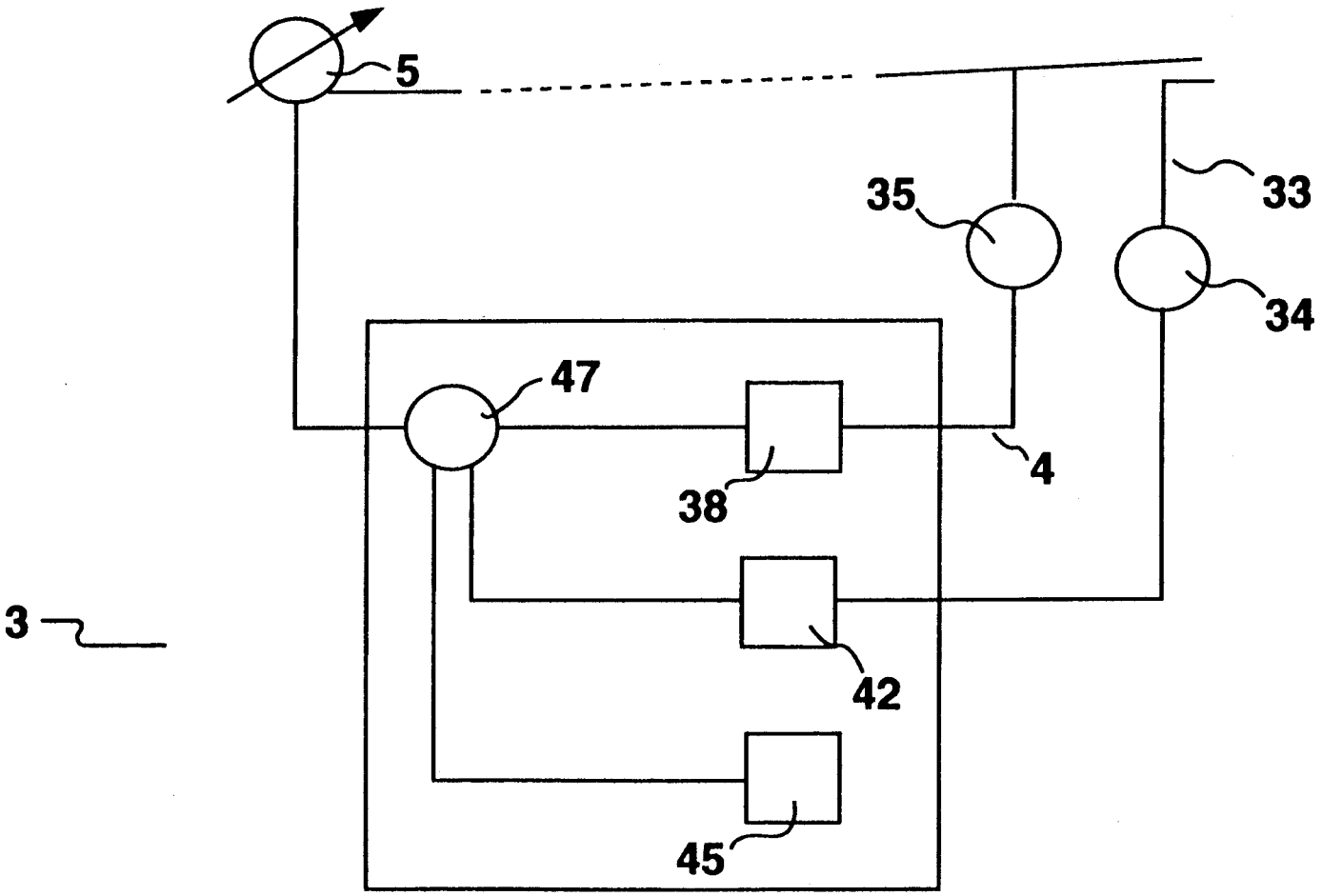
FIG. 4 is a schematic drawing of a tidal volume controller which is within the scope of the present invention.

FIG. 4 illustrates, in some detail, the tidal volume controller 3 which may be used in the respirator circuit of the present invention. The controller 3 is equipped with a frequency counter 38, a pressure switch 42, a time-cycle timer 45, and a conventional junction 47. The controller 3 is connected in such a manner so as to operate input valve 5. The tidal volume controller 3 is positioned to accept frequency signals from microphone 35 through transmitting line 4. Said signals are counted by frequency counter 38. Once the set frequency, which corresponds to a set volume of breathing gas, is reached, the frequency counter 38 signals the valve 5 to turn off. The controller 3 also is positioned to accept signals from pressure sensor 34 through transmitting line or tube 33. When the pressure sensor 34 senses a negative pressure caused by the patient's effort to inhale, pressure switch 42 signals the valve 5 to open and begin another inspiratory phase. The controller 3 is further equipped with a time-cycle timer 45 which is capable of sending a signal to both open and close the valve 5. In the event that the patient is unable to independently inhale and cause a negative pressure to operate the opening of valve 5, the time-cycle timer 45 will open the valve 5 after a preset time period. Moreover, if frequency counter 38 were to malfunction, said timer 45 would override any signals and turn valve 5 off. Hence, timer 45 creates a back-up mode for the respirator of the present invention. Conventional junction 47 may be any conventional junction which will serve the purpose of the present invention, such as a logic circuit junction.

Based on the description set forth, one is able to realize how the respirator within the scope of the invention is extremely reliable and easily adaptable to the needs of any patient.

The respirator circuit of the present invention can be produced to easily fit into a relatively small compartment, such as a small box having the measurements of 3 inches by 3 inches by 6 inches. Hence, this respirator is much smaller than the conventional volume-cycled respirators that traditionally make use of bellows or pistons, and are accompanied by a bulky electric motor.

The respirator circuit herein has numerous advantages over those already on the market. Some of the advantages include lower cost, smaller size, lighter in weight, improved reliability and ease of maintenance.

Although the invention has been described with reference to specific embodiments and drawings, it is to be understood that the invention is not limited to those precise embodiments, and that various changes and modifications may be effected by one skilled in the art without departing from the scope or spirit of the present invention.

We claim:

1. A fluidic volume-cycled respirator circuit which contains no piston-bellows assembly, said fluidic volume-cycled respirator comprising a breathing gas source;

an input valve connected to said breathing gas source;

a property independent fluidic oscillator flowmeter which is connected to said input valve and directly to a patient;

a means which transmits gas flow frequency signals from the flowmeter to a tidal volume selection controller;

a tidal volume selection controller which is connected to said means and to said input valve; and a return transmitting line equipped with a pressure sensor running from the patient to said tidal volume selection controller.

2. A fluidic volume-cycled respirator circuit in accordance with claim 1, wherein said tidal volume selection controller is electronic.

3. A fluidic volume-cycled respirator circuit in accordance with claim 1, wherein said tidal volume selection controller comprises a frequency counter, a pressure switch, and a time-cycle timer.

4. A fluidic volume-cycled respirator circuit in accordance with claim 1, wherein said fluidic oscillator flowmeter is a true volume flowmeter.

5. A fluidic volume-cycled respirator circuit in accordance with claim 1, wherein said flowmeter has no moving parts.

6. A method for accommodating the complete respiratory needs of a patient wherein said method comprises providing a breathing gas source connected to a breathing gas inlet valve;

opening said gas inlet valve so as to allow breathing gas to be forced therethrough and subsequently through a property independent, fluidic oscillator flowmeter;

delivering said breathing gas exiting from said fluidic oscillator flowmeter directly to said patient;

monitoring the flow of said breathing gas by a transmitting means which transmits the oscillator frequency count of said breathing gas to a tidal volume controller;

closing said valve once a preset oscillator frequency count is reached;

sensing negative pressure produced by an inspiratory effort from said patient using a pressure sensor;

communicating said negative pressure to said total volume controller which instructs aid breathing gas inlet valve to open; and repeating the breathing cycle;

wherein said flowmeter converts the breathing gas flow rate to a frequency signal which is converted into said frequency counts by the use of said transmitting means; and wherein said tidal volume controller operates said breathing gas inlet valve causing said valve to close once said preset oscillator frequency count is reached.

* * * * *